United States Patent [19]
Wacks

[11] Patent Number: 5,709,668
[45] Date of Patent: *Jan. 20, 1998

[54] AUTOMATIC MEDICAMENT INJECTOR EMPLOYING NON-CORING NEEDLE

[75] Inventor: Jonathan L. Wacks, Forest Hills, N.Y.

[73] Assignee: Senetek PLC, Maryland Heights, Mo.

[*] Notice: The term of this patent shall not extend beyond the expiration date of Pat. No. 5,354,287.

[21] Appl. No.: 465,790

[22] Filed: Jun. 6, 1995

Related U.S. Application Data

[63] Continuation-in-part of Ser. No. 956,952, Oct. 5, 1992, abandoned, which is a continuation-in-part of Ser. No. 740,843, Aug. 6, 1991, Pat. No. 5,360,410, which is a continuation-in-part of Ser. No. 641,752, Jan. 16, 1991, Pat. No. 5,354,287.

[51] Int. Cl.$^6$ .................................................. A61M 5/00
[52] U.S. Cl. .................. 604/232; 604/135; 604/196; 604/197; 604/201; 604/239; 604/240; 222/326
[58] Field of Search .................. 128/DIG. 4; 604/232, 604/234, 194, 195, 196, 200, 201, 202, 213, 110, 156, 137, 138–139, 403, 205–206, 197, 121–123, 130, 411, 412, 413–416, 233–237, 239–240, 144, 146, 171, 272, 274, 905, 131, 134, 135, 136; 222/326, 386; 141/27, 329, 330, 383, 385, 386

[56] References Cited

U.S. PATENT DOCUMENTS

| | | |
|---|---|---|
| 2,345,301 | 3/1944 | Smith . |
| 2,634,726 | 4/1953 | Hanson . |
| 2,701,566 | 2/1955 | Krug . |
| 2,817,372 | 12/1957 | Barr, Sr. et al. . |
| 2,832,339 | 4/1958 | Sarnoff et al. . |
| 2,876,770 | 3/1959 | White . |
| 2,989,053 | 6/1961 | Hamilton . |
| 3,066,670 | 12/1962 | Stauffer . |
| 3,119,391 | 1/1964 | Harrison . |
| 3,136,313 | 6/1964 | Enström et al. . |
| 3,181,336 | 5/1965 | Schofield . |
| 3,182,660 | 5/1965 | Weydanz et al. . |
| 3,368,558 | 2/1968 | Sarnoff et al. . |
| 3,395,704 | 8/1968 | Frey et al. . |
| 3,702,609 | 11/1972 | Steiner . |
| 3,742,948 | 7/1973 | Post et al. . |
| 3,882,849 | 5/1975 | Jamshidi . |
| 3,923,059 | 12/1975 | Ogle . |
| 4,056,177 | 11/1977 | Ahlen et al. . |
| 4,108,177 | 8/1978 | Pistor . |
| 4,178,928 | 12/1979 | Tischlinger . |
| 4,316,463 | 2/1982 | Schmitz et al. . |
| 4,328,802 | 5/1982 | Curley et al. . |
| 4,394,863 | 7/1983 | Bartner . |
| 4,411,661 | 10/1983 | Kerstent ................................. 604/411 |
| 4,499,148 | 2/1985 | Goodale et al. . |
| 4,537,593 | 8/1985 | Alchas ................................. 604/411 |

(List continued on next page.)

*Primary Examiner*—Michael Powell Buiz
*Assistant Examiner*—Ronald K. Stright, Jr.
*Attorney, Agent, or Firm*—Fitch, Even, Tabin & Flannery

[57] ABSTRACT

An automatic medicament injector employing a non-coring needle having side port geometry optimized to minimize or eliminate the coring of a rubber seal or septum when impaled by the internal needle tip of the cannula. The geometry avoids direct exposure of the butt end face of the needle to the rubber seal by providing a crimp to the material at the butt end and openings in the side thereof using electro-discharge machining (EDM) processes providing plural openings therein for introduction of medicament or aspiration through the side port geometry. The automatic medicament injector structure facilitates administration of a medicament to a predetermined target tissue avoiding exposure of the medicament or drug to tissues which would undesirably be damaged by such exposure. A needle housing assembly is disposed in a cylindrical bore of the injector cartridge wherein actuation causes the needle housing assembly to move to a widened second end of the cartridge having a needle housing assembly residence chamber for receiving the needle housing assembly when the needle housing assembly and the ampule are a predetermined distance apart.

16 Claims, 6 Drawing Sheets

U.S. PATENT DOCUMENTS

| | | | |
|---|---|---|---|
| 4,553,962 | 11/1985 | Brunet | 604/198 |
| 4,617,016 | 10/1986 | Blomberg | 604/155 |
| 4,664,653 | 5/1987 | Sagstetter et al. | 604/197 |
| 4,689,042 | 8/1987 | Sarnoff et al. | 604/89 |
| 4,693,706 | 9/1987 | Ennis, III | 604/87 |
| 4,710,180 | 12/1987 | Johnson | 604/274 |
| 4,719,825 | 1/1988 | LaHaye et al. | |
| 4,723,937 | 2/1988 | Sarnoff et al. | 604/90 |
| 4,755,169 | 7/1988 | Sarnoff et al. | 604/51 |
| 4,767,413 | 8/1988 | Haber et al. | 604/198 |
| 4,781,700 | 11/1988 | Vicario | 604/234 |
| 4,790,830 | 12/1988 | Hamacher | 604/274 |
| 4,808,184 | 2/1989 | Tepic | 604/56 |
| 4,813,936 | 3/1989 | Schroeder | 604/195 |
| 4,834,152 | 5/1989 | Howson et al. | 604/414 |
| 4,834,717 | 5/1989 | Haber et al. | 604/193 |
| 4,908,022 | 3/1990 | Haber | 604/195 |
| 4,931,040 | 6/1990 | Haber et al. | 604/110 |
| 4,936,833 | 6/1990 | Sams | 604/232 |
| 4,950,246 | 8/1990 | Muller | 604/154 |
| 4,955,869 | 9/1990 | Bin | 604/195 |
| 4,968,299 | 11/1990 | Ahlstrand et al. | 604/90 |
| 4,968,303 | 11/1990 | Clarke et al. | 604/187 |
| 4,983,164 | 1/1991 | Hook et al. | 604/87 |
| 4,995,870 | 2/1991 | Baskas | 604/110 |
| 5,092,842 | 3/1992 | Bechtold et al. | 604/135 |
| 5,094,148 | 3/1992 | Haber et al. | |
| 5,098,382 | 3/1992 | Haber et al. | 604/110 |
| 5,100,390 | 3/1992 | Lubeck et al. | 604/274 |
| 5,102,393 | 4/1992 | Sarnoff et al. | 604/136 |
| 5,112,317 | 5/1992 | Michel | 604/208 |
| 5,114,406 | 5/1992 | Gabriel et al. | 604/236 |
| 5,125,899 | 6/1992 | Frignoli | 604/110 |
| 5,221,262 | 6/1993 | Kite | 604/110 |
| 5,226,900 | 7/1993 | Bancsi et al. | 604/414 |
| 5,232,458 | 8/1993 | Chen | 604/195 |
| 5,354,287 | 10/1994 | Wacks | 604/232 |
| 5,509,912 | 4/1996 | Vaillancourt et al. | 604/88 |

AUTOMATIC MEDICAMENT INJECTOR EMPLOYING NON-CORING NEEDLE

This application is a Continuation-In-Part of application Ser. No. 07/956,952, filed Oct. 5, 1992, now abandoned, which is a Continuation-In-Part of application Ser. No. 07/740,843, filed Aug. 6, 1991, now U.S. Pat. No. 5,360,410, which is a Continuation-In-Part of application Ser. No. 07/641,752, filed Jan. 16, 1991, now U.S. Pat. No. 5,354,287. The aforementioned applications, Ser. Nos. 07/956,952, 07/740,843 and 07/641,752, are hereby incorporated by reference.

BACKGROUND OF THE INVENTION

The present invention relates to automatic injection devices, aspiration devices, cartridge vials, and to non-coring needles for use therewith for medical and research purposes and more particularly, to devices designed for injecting medicines and other fluids into human beings and other subjects using a hollow injection needle. The invention also relates to methods of administering fluid medications by injection with a device of the invention, specifically an automatic medicament injector employing a non-coring needle.

In the conventional medical procedure for injecting medicines or for aspirating blood or fluids, a syringe is used which typically has an exposed hollow injection/aspiration needle, such as a standard hypodermic needle or cannula. Needles are repugnant to many patients, particularly those who must have regular injections of medicine or blood samples taken. A related problem is that of the dangers of exposing a needle to the atmosphere or contaminants prior to its being used in giving an injection of medication or withdrawing of body fluid. Not only is there danger of wounds to user, personnel and patients from the exposed needle tip, but there is the danger that the exposed needle will become contaminated by airborne or aerosol borne microbial and other contaminants and infect the patient eventually injected. This danger is particularly acute in hospitals and other medical treatment areas where strains of antibiotic-resistant microbes endemically contaminate the air and all exposed surfaces. Contact with non-sterile air is a certainty with conventional, exposed-needle, syringe technology because, in this technology, needles are routinely exposed to the air or surfaces for some discrete amount of time during use. Also, in emergency situations such as military combat, natural disasters, or industrial accidents, the unused needle may be left exposed to such contaminants by untrained, harried or inexperienced personnel.

Another common problem in conventional syringe/injection technology is that relating to improperly given injections. The differences in the rate which a needle must travel during insertion into and withdrawal from the subject's tissues and the rate at which a syringe piston must be operated in order to inject or aspirate fluid in a painless manner are substantial. The techniques of various medical personnel in using conventional syringes can vary. Techniques vary according to the position of the subject, how that portion of the subject's anatomy which is to be injected is held, and by the various individual techniques of medical personnel. This problem is particularly acute with respect to untrained or inexperienced personnel. When a needle is inserted too slowly, needless pain results. These problems are overwhelmingly due to the difficulty of operating a syringe and needle in a manner which appropriately varies the rates of needle insertion and withdrawal and the rates of fluid injection and aspiration.

An additional problem in the field is that of dosage management. For subjects who give themselves injections, either because they require regular doses of injected pharmaceuticals or because medical personnel are not available, it is critical to ensure that dosages are correct. Diabetic subjects, particularly diabetics who suffer from the related condition of blindness, often find themselves in such situations. Other blind people are similarly in need of a product which ensures that both the type of medication and its dosage are correct for their specific needs. Similarly, soldiers in the field, travelers requiring regular injectable medications, and subjects in emergency situations where self-injection is necessary often have difficulty administering the proper dosage of a given drug and often have difficulty in using a conventional syringe. Such problems are also compounded by darkness or poor lighting conditions in battlefield, power failure, and other crisis or emergency situations.

For subjects injecting themselves at home, in emergency situations, or in combat, it is virtually impossible to perform the correct procedure. Similarly, personnel who are untrained in medical injection procedures but must give injections because of crisis or emergency situations are much more likely to incorrectly administer a substance, either by administering an incorrect dosage or administering by placing the needle so that its tip is positioned at an inappropriate site (e.g., so that the substance is injected directly into the blood stream rather than intramuscularly).

Accordingly, automatic injectors utilizing various mechanical or electro-mechanical actuation mechanisms and the like have been developed allowing individuals including subjects themselves to provide injection of medications. Since actuator mechanisms for such automatic injectors often employ a compressed spring which is released to rapidly cause the rubber seal or septum of a medication cartridge or ampule to rapidly impale itself upon the butt end of the cannula, a problem has been observed in that a rubber "core" is often cut out of the rubber seal of the medication cartridge. As a result, the core can either block the inner diameter of the needle completely, or the core itself may be injected therethrough and into the patient along with the medication. With the high speeds at which the internal needle is driven into the rubber seal of the medication cartridge ampule, it has been observed that the rubber seal, in this setting, no longer acts in a visco-elastic fashion, there being insufficient time for any relaxation or hysteresis effects of the material. Thus, the butt end of the internal needle when impaled upon the rubber seal in the automatic injector environment, naturally cores the rubber seal material itself causing such material to move through the needle or perhaps become lodged therein.

In the past, needles have been used having a "Huber" point to solve the coring problem by employing a curved needle with an opening at 90 degrees to the rubber seal. Nonetheless, in the environment of automatic injectors, it was found that the "Huber" point was unsuccessful in solving the problem. It has been observed that coring still results despite the curved needle structure, and a rubber core is introduced at the opening on top of the "Huber" point because the butt end face of the needle is still exposed directly to the rubber seal.

To this end, various needle geometries are found in the art for preventing or limiting the coring of the rubber seal. However, conventional prior art approaches were found unsatisfactory for use in conjunction with automatic injectors wherein the impaling of the rubber seal occurs with such rapidity and force. Accordingly, it would be desirable to determine and obtain a needle geometry providing a non-coring needle for use with automatic medicament injectors.

SUMMARY OF THE INVENTION

It is an object of the present invention to provide concealment of an injection needle at all stages of use, to maintain sterility of an injection needle at all stages of use by providing means whereby the needle, prior to contact with the skin of a patient for penetration therethrough, is never exposed to any potentially contaminating surfaces, aerosols or airborne particles or microbes.

It is another object of the present invention to provide an injection vial which eliminates the dangers of infection or injury resulting from accidental contact with exposed needles, and to provide a sanitarily disposable injection vial which can be safely discarded without the need for special equipment or containers and which can be safely and sanitarily disposed of in non-hospital, rugged, or emergency environments.

It is also an object of the present invention to provide an ampule or cartridge for dispensing fluid medication which can be filled by the use of conventional pharmaceutical packaging machinery, thus avoiding the substantial expense which would be required for the development and production of non-conventional packaging methods and machinery.

It is a further object of the present invention to reduce the risk of an improperly administered injection by providing means for precisely and automatically controlling the rate of needle insertion and the rate of medicine injection, and the rate of fluid aspiration.

It is a further object of the invention to reduce the risk that an incorrect drug will be administered to a subject or be self-administered by a subject.

It is an additional object of the present invention to provide means to administer a drug to a pre-selected target tissue and avoid exposure of the drug to tissues which would be undesirably damaged by such exposure.

It is yet another object of the present invention to provide a means for giving or self-administering penile injections of drugs with a minimum of pain and apprehension on the part of the male.

Furthermore, it is another object of the invention to provide an automatic medicament injector employing a non-coring needle.

It is another object of the invention to provide "side port" geometry in the internal needle of an automatic injector to eliminate direct butt end face exposure of the needle, such side port geometry being optimized to minimize or eliminate the coring problem.

It is a still further object of the invention to optimize the opening area of the side port geometry with respect to the inner diameter of the needle, to provide a non-coring needle appropriately varying the rate of fluid injection and aspiration.

In accordance with the objectives of the invention, a vial for fluid injection is provided. The injection vial is a double-ended cartridge, having a first end and a second end, the cartridge having a cylindrical bore defined by a wall extending between the first end and the second end, the bore being suitable for storing a fluid charge to be expelled therefrom. The cartridge is provided with a puncturable end cap which is rigidly attached and sealed to the second end of the cartridge and which comprises a needle guide. The cartridge is also provided with a hollow injection needle having an external tip and an internal tip, the internal tip being rigidly attached to and passing towards the vial, and the external tip extending toward the end cap without protruding therefrom. It is preferred that the puncturable end cap be made of self-sealing material, although this is not necessary for practicing the invention.

It is also preferred that the external end of the injection needle is disposed within the puncturable end cap of the cartridge a sufficient distance to provide a microbe-impermeable seal without protruding therefrom.

The internal tip of the hollow injection needle is provided with a crimped butt end and one or more side port openings such that the crimped end of the internal tip is used to impale upon the rubber seal such that no coring results in material within the hollow injection needle. The side port geometry of the needle is provided with an opening area with respect to the inner diameter of the hollow injection needle to facilitate appropriate variations in the rates of fluid injection and aspiration. In providing the precise side port geometry openings in the hollow injection needle, electrical discharge machining (EDM) is utilized with available EDM tooling for making a variety of opening-in small gage needles.

In accordance with other objects of the invention, a mechanically actuated cartridge vial for fluid injection is provided. The mechanically actuated cartridge vial is a cartridge, having a first end and a second end, the cartridge having a cylindrical bore which is widened at the second end of the cartridge to form a cylindrical needle housing assembly residence chamber for reversibly receiving a needle housing assembly, and a puncturable end cap, the end cap sealing the second end of the cartridge and having a needle guide disposed therein.

The mechanical actuator component of the invention comprises an actuator housing, the housing having a first end and a second end, the first end adapted for receiving the cartridge vial and the second end adapted for operating the cartridge vial and actuator. A piston driver is slidably seated in the housing, the driver having a piston face for contacting the ampule piston, a transfer surface for transferring propelling force from the housing to the driver, and a trigger end for releasably engaging the second end of the actuator housing.

Also provided in the actuator housing are a detent or seat flange in the second firing end for releasably engaging the piston driver, a detent release or release flange in the second firing end for disengaging the piston driver from the second end, and a propulsion mechanism (e.g., a spring) disposed between the transfer surface and the second end of the housing for driving the piston driver toward the puncturable end cap when the detent release or release flange is triggered.

A needle housing assembly is disposed in the cylindrical bore of the cartridge, the needle housing assembly comprising a housing, a hollow injection needle rigidly attached to the housing and having an internal end and an external end, the internal end of the needle extending through the needle assembly housing toward the puncturable ampule end stopper, and the external end of the hollow injection needle extending toward the puncturable end cap of the cartridge without protruding therefrom; and an actuator for engaging the cartridge vial and for propelling the ampule toward the puncturable end cap and for propelling the piston within the ampule toward the ampule end stopper to inject a fluid. The needle housing assembly disposed within the cartridge is provided with locking means for irreversibly locking the needle assembly housing to the ampule when the needle housing assembly and the ampule are a predetermined distance apart.

The automatic medicament injector is provided as employing a non-coring needle having side port geometry optimized to minimize or eliminate the coring of a rubber or septum when impaled by the internal needle tip of the non-coring needle. The geometry avoids direct exposure of the butt end face of the needle to the rubber seal by providing a crimp to the material at the butt end and openings in the side thereof using an EDM process providing plural openings therein for the introduction of medicament through the side port geometry.

A more detailed description of the preferred embodiments of the invention, and further objects and advantages of the invention are set forth in the drawings and in the detailed description which follows and in the claims annexed to informing a part of this specification. The invention itself is defined with particularity in the claims.

BRIEF DESCRIPTION OF THE DRAWINGS

The invention will now be described with reference to the accompanying drawings, in which.

DETAILED DESCRIPTION OF THE PREFERRED EMBODIMENT

Figure 1:
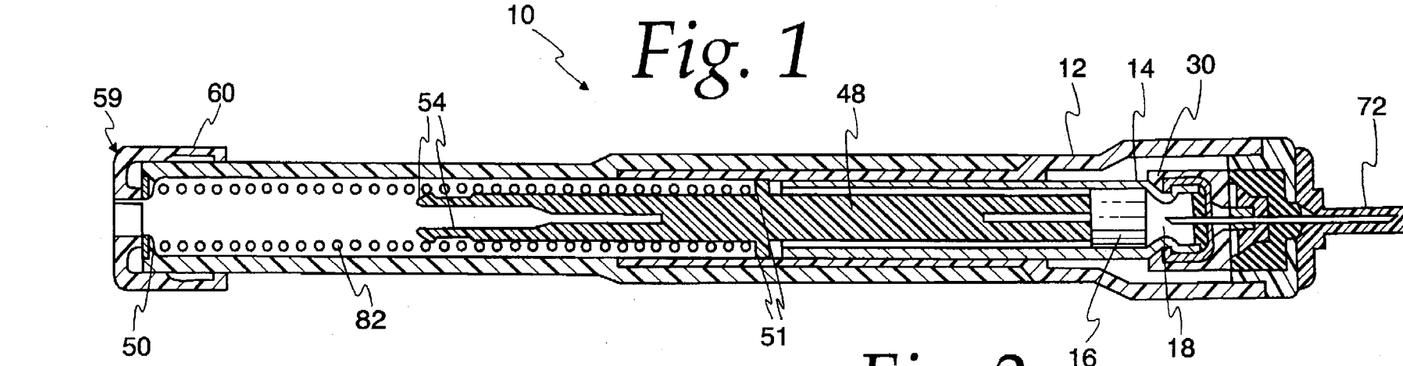
FIG. 1 illustrates an embodiment of an automatic injector in cross-section, showing a cartridge vial for use with a mechanically powered actuator mated to such an actuator and showing the relative placement of major components of the vial and actuator after firing of the actuator, completion of an injection, and covering of the exposed injection needle by the actuator safety pin for use with automatic injections in accordance with the invention.
Figure 2:
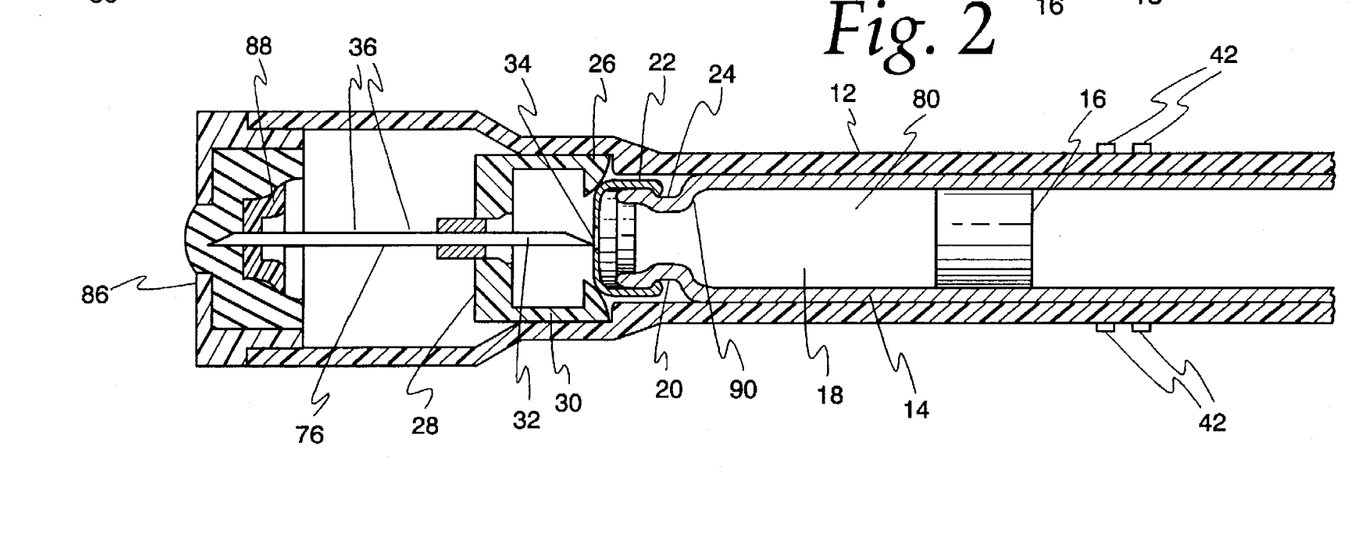
FIG. 2 is a longitudinal cross-sectional view of a cartridge vial device for use with a mechanically powered actuator showing the relative placement of the ampule, cartridge, needle housing assembly, and other components.

FIGS. 1–4 illustrate an embodiment of a mechanical automatic injector 10 according to the invention. With reference to FIG. 1, an embodiment of the cartridge vial of the present invention intended for injections where no aspiration is necessary is illustrated. The automatic injector 10, as illustrated, is shown as having been actuated, the process of which is described as follows. Cartridge 12 is provided with slidable ampule 14 having piston 16 for expelling fluid from fluid chamber 18 and having a second ampule portion 20 which is smaller in outer diameter than a third ampule portion 22, the transition area therebetween forming an engaging surface 24 for engaging flanges 26 of a needle housing assembly 28 (FIG. 2). The cartridge 12 thus has first and second ends and a cylindrical bore which is widened at the second end of the cartridge to form a cylindrical needle housing assembly residence chamber for reversibly receiving a needle housing assembly wherein the needle housing assembly disposed in the cylindrical bore of the cartridge comprises a hollow injection needle rigidly attached to a housing; and an actuator for engaging said cartridge vial and for propelling said ampule toward said puncturable end cap and for propelling said piston within said ampule toward said ampule end stopper to eject the fluid. Needle assembly housing 28 is provided with needle assembly housing walls 30 of sufficient length that when the flanges 26 irreversibly lock or capture third portion 22 of ampule 14, a needle tip 32 has already punctured a puncturable ampule end stopper 34. Needle housing assembly walls 30 are of a sufficient diameter such that expansion of walls 30 cannot occur until needle housing assembly 28 is pushed into needle housing assembly residence chamber 36 by the movement of slidable ampule 14.

Figure 3:
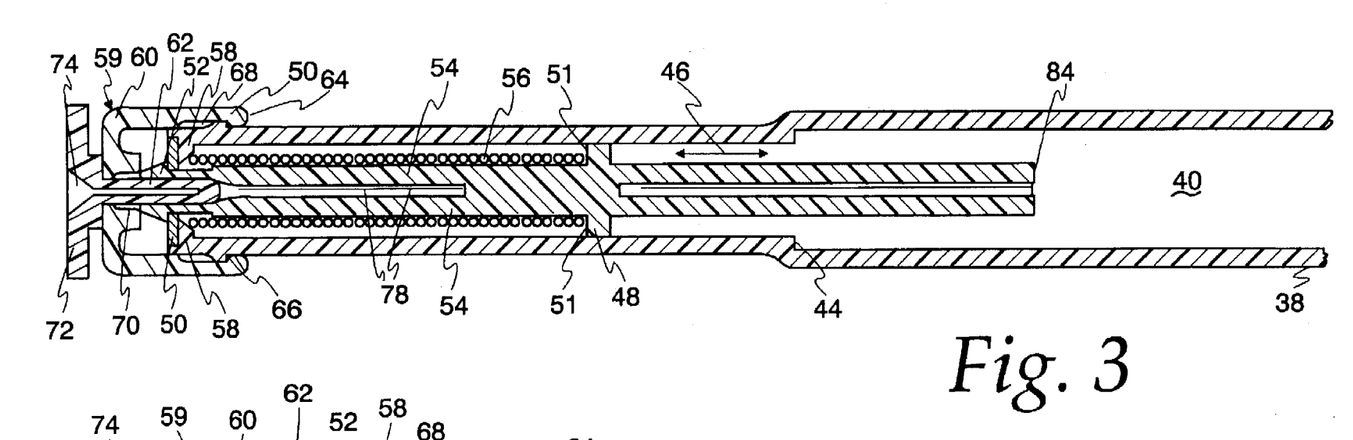
FIG. 3 is a longitudinal cross-sectional view of a spring-powered cartridge vial actuator before insertion of a cartridge vial, and showing the relative positions of the actuator housing, piston driver, spring, and firing cap assembly.
Figure 4:
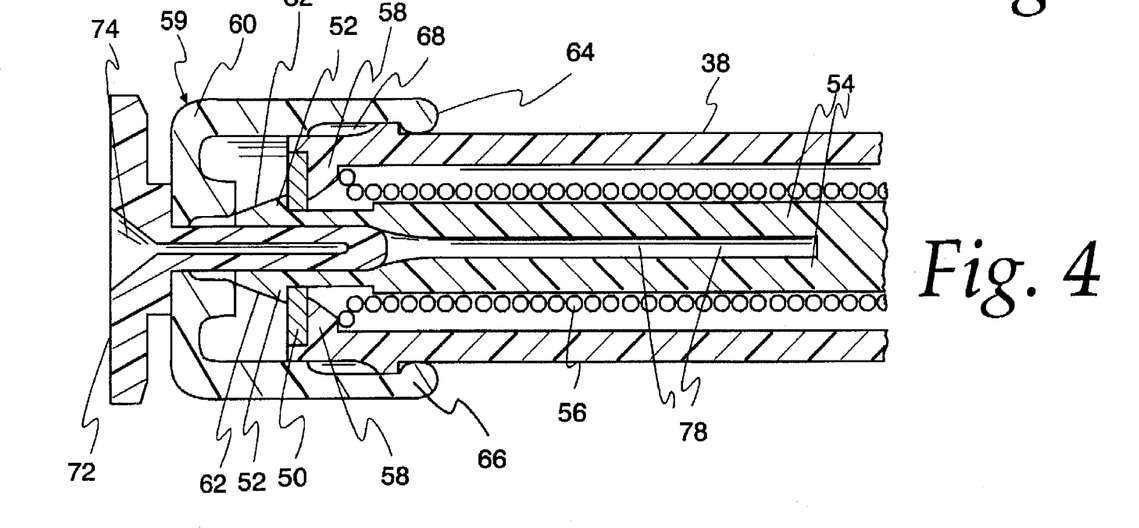
FIG. 4 is an enlarged view of the firing cap assembly shown in FIG. 3.

With reference to FIGS. 2–4, details of the described embodiment of the cartridge vial and actuator of the automatic injector 10 are shown. A cartridge vial actuator housing 38 is provided with a cartridge vial receiving chamber 40 shown in FIG. 3 for receiving a cartridge vial of the type as shown specifically in FIG. 2 is also provided with cartridge vial locking projections and indentations 42 for engaging and positioning the cartridge vial with respect to the actuator housing 38. Cartridge vial actuator housing 38 is also provided with a cartridge vial positioning abutment 44 for holding the cartridge vial in a predetermined position. Cartridge vial actuator housing 38 is also provided with a piston driver residence chamber 46 wherein an elongated piston driver 48 is slidably seated.

Piston driver 48 is releasably attached through a piston driver flange seat 50 in the body of housing 38 by piston driver release flanges 52 which are attached to piston driver release arms 54 as shown in the enlarged view of FIG. 4. Piston driver 48 is also provided with piston driver spring 56 which is coiled around piston driver release arms 54 in a compressed condition and abutting on a piston driver spring shoulder and housing spring shelf 58 thus biasing the piston driver 48 toward cartridge vial receiving chamber 40. The piston driver 48 has a piston face, transfer surface 51 and trigger end 59, and the propulsion mechanism is connected between the transfer surface 51 and the second end of said housing, which thus provides a driving force propelling the piston driver toward the puncturable end cap when the triggering end 59 of the elongated piston driver is triggered from the detent release or release flange 52.

Cartridge vial actuator housing 38 is also provided with a firing cap 60 having flange constriction surfaces 62 which loosely abut piston driver release flanges 52. Firing cap 60 is also provided with a firing cap attachment lip 64 which surrounds a firing cap engagement ring 66 and is further provided with a firing cap slot 68 which permits the longitudinal movement of the firing cap 60 with respect to the cartridge vial actuator housing 38. Firing cap 60 is also provided with a firing cap safety pin aperture 70 for receiving safety pin/needle cover 72 therethrough.

It is thus clearly shown in FIG. 1 that the piston driver release arms 54 and piston driver flanges 52 are held seated or locked on the piston driver flange seat 50 by the expansion of a piston driver safety pin aperture 78 by a safety pin/needle cover 72. Safety pin/needle cover 72 is also provided with a needle cover aperture 74 which can be used to cover the protruding portion of injection needle 76 after an injection.

The mechanically actuated cartridge vial of the invention, as shown in FIGS. 1-4, operates as described herein below.

The space in ampule fluid chamber 18 is filled with a charge 80 of fluid medicament to be injected into a subject. Cartridge vial housing 12 is disposed within cartridge vial receiving chamber 40 of cartridge vial actuator housing 38 in a position determined by cartridge vial position abutment 44 and cartridge vial locking projections and indentations 42.

The force of a compressed piston driver spring 82 is released by the following actions: safety pin/needle cover 72 disposed within piston driver safety pin void 70 is withdrawn from its void through firing cap safety pin aperture 78. Firing cap 60 is then depressed in the direction of cartridge vial receiving chamber 40 thus causing angled flange constriction surfaces 62 to impinge upon the angled surfaces of piston driver release flanges 52 thereby causing the movement of those flanges toward each other and permitting flanges 52 to be pulled through an aperture in piston driver flange seat 50 by the force of expanding piston driver spring 56 thus causing movement of piston driver 48 in the direction of a cartridge vial end cap 86. The movement of piston driver 48 causes a cartridge vial piston contact face 84 to contact a piston 16 disposed above fluid chamber 18 in ampule 14 thus applying hydraulic pressure through fluid charge 80 to propel slidable ampule 14 toward end cap 86.

Thus, continued movement of piston driver 48 causes movement of needle assembly housing 28 also in the direction of end cap 86 so that injection needle 76 punctures end cap 86 and needle assembly housing 28 enters needle assembly housing residence chamber 36 until the needle assembly housing is stopped by a needle guide 88 disposed within end cap 86. Continued pressure on the piston 16 then causes the expansion of needle assembly housing flanges 26 and the puncture of puncturable ampule end stopper 34 by needle internal end 32.

Continued pressure on the piston 16 by expanding piston driver spring 56 communicated through piston driver 48 causes ejection of fluid charge 80 through hollow injection needle 76 until piston 86 bottoms out against ampule internal abutment 90. The mechanically actuated cartridge vial is then removed from a subject target area and safety pin/needle cover 72 is then placed over the exposed portion of extended injection needle 76 to prevent unwanted or unintentional punctures by the needle. Thus, no part of needle 76 need ever be exposed to any environment other than the subject's tissues or the inside of the cartridge vial before injection. The needle housing assembly and an ampule storing a fluid charge disposed within a cartridge such that the needle housing assembly is physically separated from the ampule prior to injection. This serves a number of ends, including the ability to change ampules (change medicines) at any time prior to use and, particularly, the ability to keep the hollow injection needle of the needle housing free from fluid or medicine prior to injection. Advantageously, the cartridge has an interior bore wall that widens to form a needle housing assembly, which in conjunction with the needle housing assembly employed, achieves injection of the needle first, prior to introduction of medicine, and allows the needle housing assembly to move within the bore wall of the cartridge to a widened bore wall (needle housing assembly residence chamber). In turn, this propels the hollow injection needle outward from a puncturable end cap sealing the end of the cartridge allowing the injection needle to locate itself within targeted tissue prior to introducing fluid through the injection needle. Fluid injection occurs only when the needle housing assembly is positioned within the needle housing assembly chamber where the walls of the needle housing assembly may widen allowing the ampule's puncturable end stopper to impale itself upon the internal end of the injection needle.

A preferred material for the actuator housing, cartridge housing, needle assembly housing, firing cap, needle guide, end cap, safety pin/needle cover, and piston driver is radiation resistant polypropylene known in the medical arts. However, it can clearly be seen that many other materials which are standard in the medical and dental packaging and hypodermic syringe art such as plastics, including glass-filled plastics, carbon fiber composites, rubber, synthetic and non-synthetic materials know in the art and nylon/carbon fiber composites. A preferred material for the injection needle and piston driver flange seat is stainless steel. However, any other reasonable substitute material such as glass, ceramics, and carbon fiber composites are acceptable.

Similarly, a preferred material for the piston driver is a nylon/carbon fiber composite, although numerous other materials having sufficient resilience, rigidity, and tensile strengths are acceptable to practice the present invention.

Preferred materials for the ampule piston, cartridge end cap, and puncturable shield include natural or synthetic rubber, silicone rubber, glass-filled silicone rubber, and various plastics so long as the desired characteristics of sealability, puncturability, and manufacture to precise tolerances are achievable. A preferred material for the puncturable ampule end stopper is a rubber disk or membrane securely attached and sealed to the ampule by an aluminum cover as is standard in the medical and dental arts.

A preferred material for the ampule is silicone treated USP glass, although many plastics and composite materials are also suitable as known in the art.

Suitable materials for the piston driver spring also include carbon steel, stainless steel, glass-filled nylon, various glasses, or any other material capable of providing biasing and propelling force in the context of the invention.

It is preferred that all components of the invention be amenable to sterilization by processes using gamma rays, electron beams, or ethylene oxide. Such materials include ABS plastics, polycarbonates, glasses and carbon fiber composites.

The needle assembly housing dimensions must be tailored with respect to the specific material used in order to achieve acceptable deformation characteristics to permit expansion of the needle assembly housing flanges under the particular amount of force transmitted from the piston driver spring. Of course, it can also be clearly seen that spring characteristics such as uncompressed length, material, and stiffness can be varied to adapt the piston driver spring for use with particular types of ampule and needle housing assemblies.

Turning now to the needle or cannula designs for use with automatic injectors as that of the embodiment described thus far. During development, a problem was encountered during the activation of the automatic injector. Specifically, as the medication cartridge impales itself onto the butt end of the cannula, a rubber "core" is cut out of the cartridge seal or septum, herein the puncturable ampule end stopper 34 as the needle tip 32 contacts therewith. The core would either block the inner diameter of the needle completely, or become injected into the patient along with the medication. High-speed photographic analysis of the injector process revealed that the entire needle activation was completed in 5 to 20 milliseconds. It was theorized therefore that because of the speeds involved, the rubber was no longer behaving in a visco-elastic fashion (there was insufficient time for any relaxation or hysteresis effects of the material). Although a variety of rubber materials were evaluated, the speed of the injection and the medication sensitivity precluded a material-based solution. Thus, it was determined that the butt end of the needle tip 32 would have to be modified in the development of a non-coring needle.

Figures 5A, 5B, 6A, 6B, 6C:
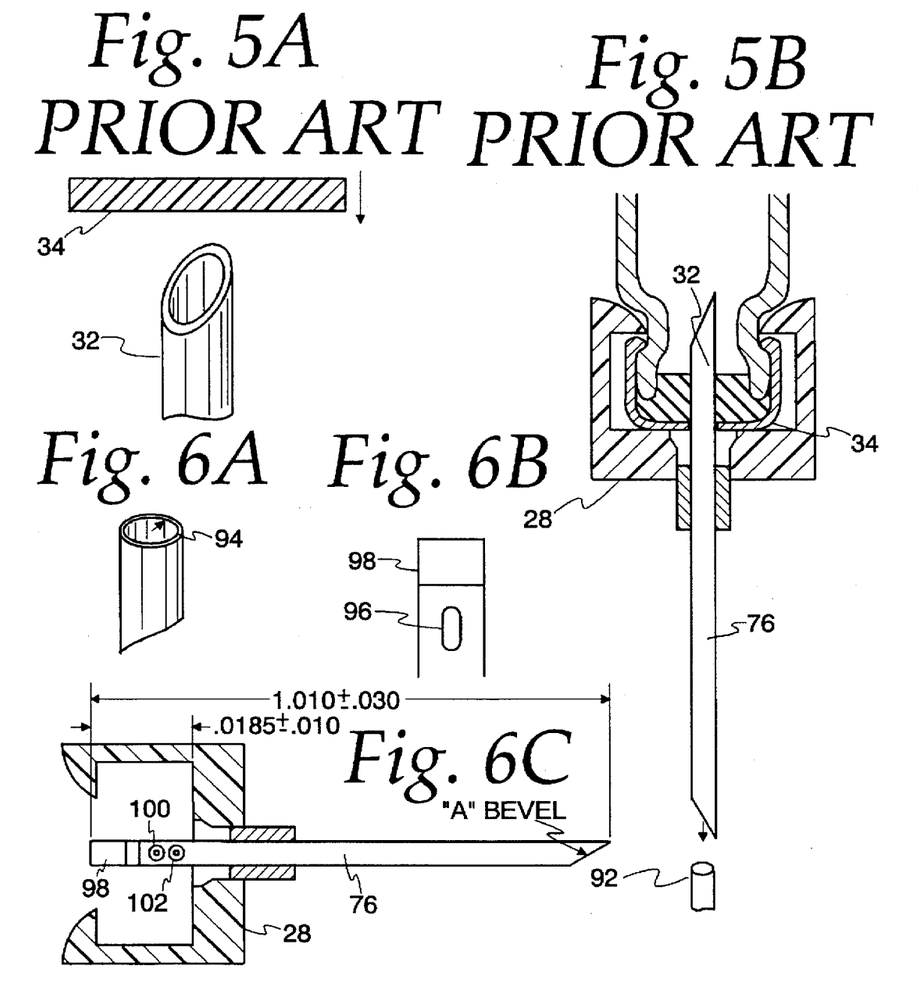
FIGS. 5A and 5B illustrate the coring problem associated with conventional internal needle butt ends employed with automatic injectors.
FIGS. 6A and 6B illustrate an open butt end needle tip and the inner diameter thereof and a crimped end with a matched slot, matching the area of the internal diameter, respectively.
FIGS. 6C, 6D and 6E show a preferred embodiment non-coring needle wherein the butt end of the internal needle tip is crimped and two (2) openings are provided in the side thereof using an EDM process to provide side port geometry for the internal tip of the hollow injection needle.

Turning now to FIGS. 5A and 5B, the basic problem is illustrated wherein as the needle tip 32 impales into the rubber seal of the puncturable ampule end stopper 34, the core 92 will block injection or the core 92 of rubber will inject itself into the patient along with the medication itself.

FIG. 6A shows a standard butt end of a hollow injection needle having an inner diameter (I.D.) defining a needle contact area or opening (Area$_1$). FIG. 6B shows a slotted opening 96 providing side port geometry wherein slot 96 may be provided as having an area equal to Area$_1$ of FIG. 6A, inner diameter 94. The hollow injection needle I.D. Area$_1$ and the sideport opening may thus be formed to define a sideport area in dependence upon Area$_1$ and a desired flow rate for said medicament, the area associated with the side port geometry being varied to enhance or impede flow rates therethrough as desired for aspiration or injection. A crimp 98 is provided giving a rugged-lacerated end to the butt end of the needle. The rugged-lacerated end is preferred over a blunt end or ball-type feature provided by a weld. Thus, the crimp 98 facilitates preventing exposure of the side port slot 96 to the rubber 34 during impalement thereof.

Figure 6D:
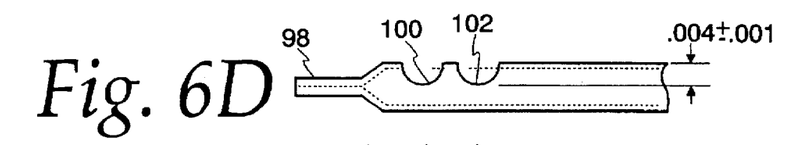
Figure 6E:
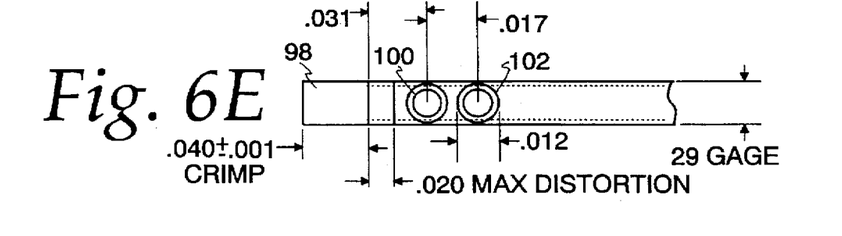

FIG. 6C shows the preferred embodiment of the needle and needle housing assembly 28 providing the non-coring needle wherein slots 100 and 102 are provided with the EDM process involving electrically biasing a work tool and using a discharge to cut forms, here in slots 100 and 102, in the work piece, the cannula. FIGS. 6D and 6E show enlarged views illustrating the crimp 98 and slots 100 and 102 of the preferred embodiment.

Although a standard grinding wheel could be utilized to make the slots 100 and 102 in the side of the cannula, the EDM tool was found more useful in making a variety of openings in a small gage product, such as the non-coring needle described herein. Because the EDM tool does not encounter traditional dimensional wear associated with traditional machining, complex shapes and geometries can be created with the EDM process. In the case of fabricating needles for the subject non-coring needle, a wire EDM tool biases a 0.010" outer diameter (O.D.) wire to cut the stainless steel needle as shown and discussed further below. The needle utilized for the cannula is 29 gage, having 0.013" O.D. and 0.0035" wall thickness. Typically, the manufacturing process involves taping 300 to 500 needles in a fixture, first cutting approximately 0.010" of material off the ends thereof to null or zero out registration of the needles, and then using the EDM process to provide one or more holes therein. Finally, the crimp 98 is provided pressing the needle ends shut. The described process may be provided by a number of needle fabricators such as CT Hypodermics of Yalesville, Conn.

Preferred dimensions relative to the crimp 98 and slots 100 and 102 are also given in FIGS. 6C, 6D, and 6E for a 29 gauge needle. As shown in FIG. 6C, the overall length from the end of the crimp 98 to the point of the needle 76 is preferably about 1.010 inches whereas the length from the end of the crimp 98 to the needle housing assembly 28 is preferably about 0.185 inches. As shown in FIGS. 6D and 6E, the preferred length of the crimp 98 is 0.040 inches with the slot 100 being preferably about 0.31 inches from the end of crimp 98. Preferably, slot 102 is located about 0.017 inches from slot 100 and the nominal diameter of the slots 100 and 102 is about 0.012 inches with a preferred depth of about 0.004 inches. As one skilled in the art will realize, these dimensions, while preferred, are not required and may be varied from the preferred dimensions contained in FIGS. 6C, 6D, and 6E. Moreover, other sized needles will, of course, have different preferred dimensions which can easily be determined by experimentation using the preferred dimensions given above and taking into account the diameter and other dimensions of the desired needle.

Figure 7A:
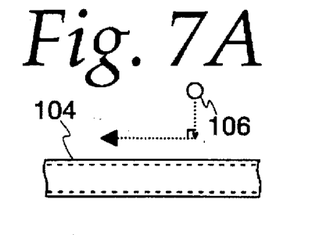
FIGS. 7A–7F illustrate various EDM process techniques for providing modified slots as side port geometries.
Figure 7B:
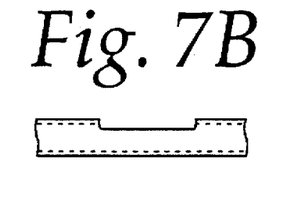
Figure 7C:
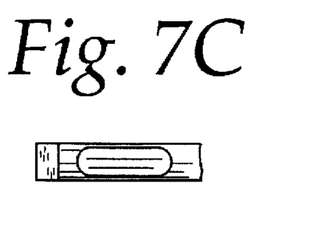

Turning to FIGS. 7A–7F, movement of an EDM wire 106 and the resulting slots created with the EDM process are illustrated. FIG. 7A illustrates downward and horizontal movement along the needle 104 to generate the slot shown in FIG. 7B and 7C. The EDM tool employs an X-Y-Z stage capable of moving in 0.00005" (50 millionths) increments. In this fashion, the wire O.D. geometry can be used to fashion an array of geometries in the needles. As discussed, the EDM process is done by placing several such needles (e.g., 300 to 500) on a work piece, supported in a clamping tool, and maintained level and flush with tape (see, e.g., FIGS. 8A and 8B, plan and side views). The simple slot of FIG. 7C may be generated as equivalent to the area of the standard butt end of the needle, as discussed in connection with slot 96 of FIG. 6B.

Figure 7D:
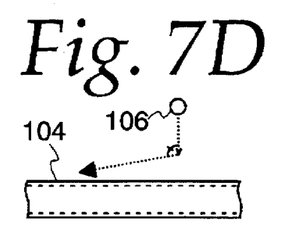
Figure 7E:
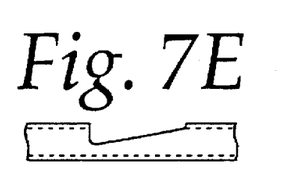
Figure 7F:
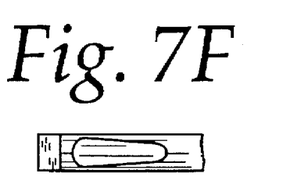

Additionally, a modified "V" geometry is illustrated in FIGS. 7D–7F wherein the EDM wire 106 is dropped to the needle 104 and moved downward and sideways in generating the slot providing a cut geometry as illustrated in FIG. 7F.

Figure 8A:
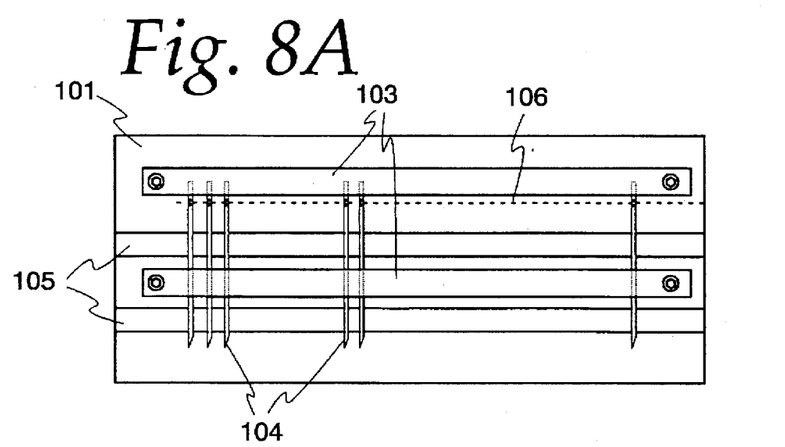
FIGS. 8A, 8B and 8C show an EDM fixture and a clamping tool for holding needles flush and level during EDM process and crimping thereof.
Figures 8B, 8C:
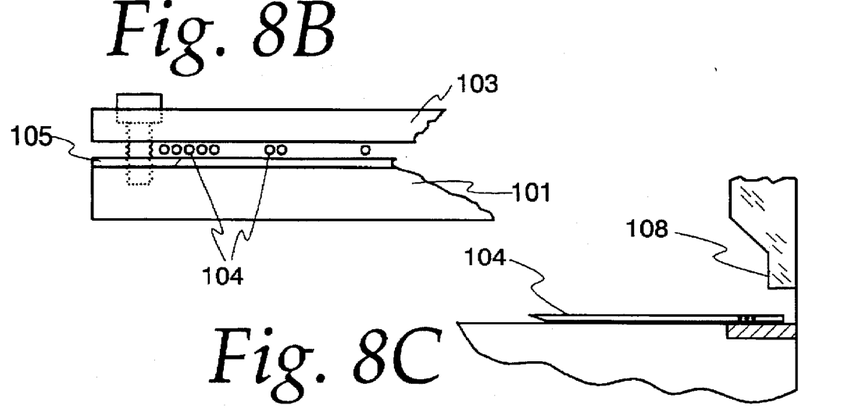

FIGS. 8A and 8B show plan and side views respectively of an EDM fixture 101 having clamping bars 103, and using tape 105 for securing the needles 104 during the formation of one or more slots therein with the EDM wire 106 (shown as a dashed line).

FIG. 8C shows a press including a Moving Ram 108 and adjustable end block 110 used to crimp the ends of the needle 104. The Moving Ram 108 on the press may be provided with an adjustable stop for modifying the characteristics of the crimp 98 generated thereby.

Figure 9A:
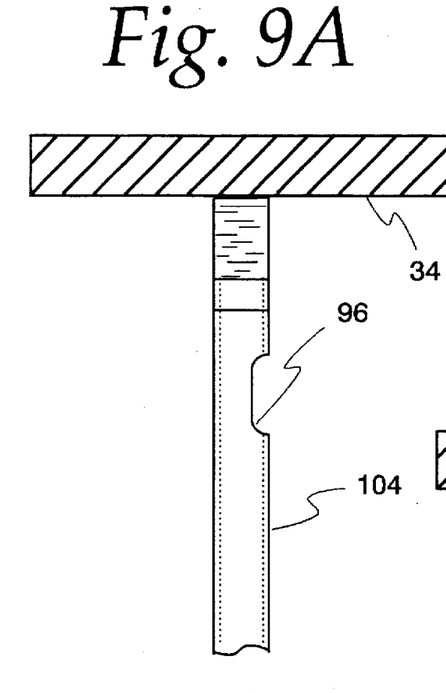
FIGS. 9A and 9B illustrate rubber fragmentation resulting from slot side port geometry.
Figure 9B:
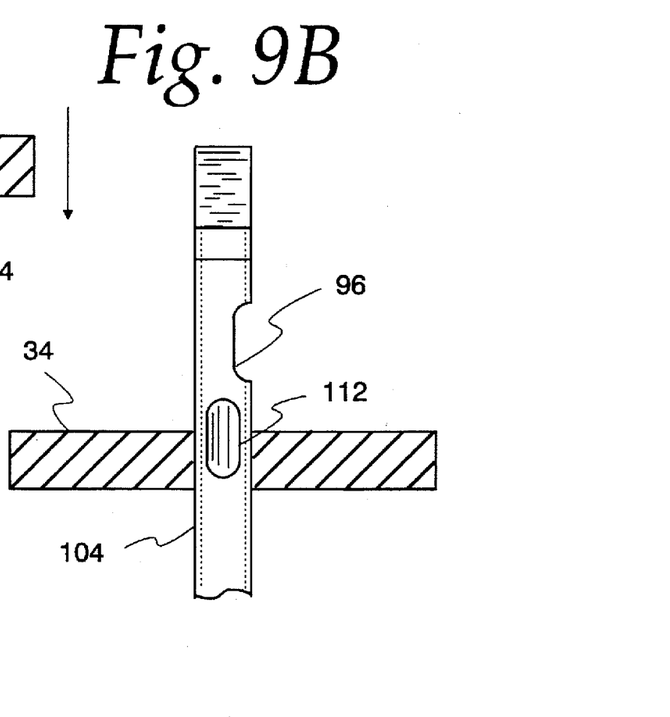
Figure 10A:
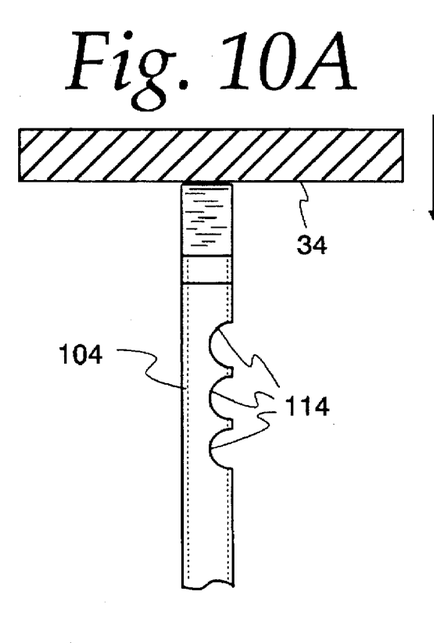
FIGS. 10A and 10B illustrate smaller rubber fragments produced with a three-hole design.
Figure 10B:
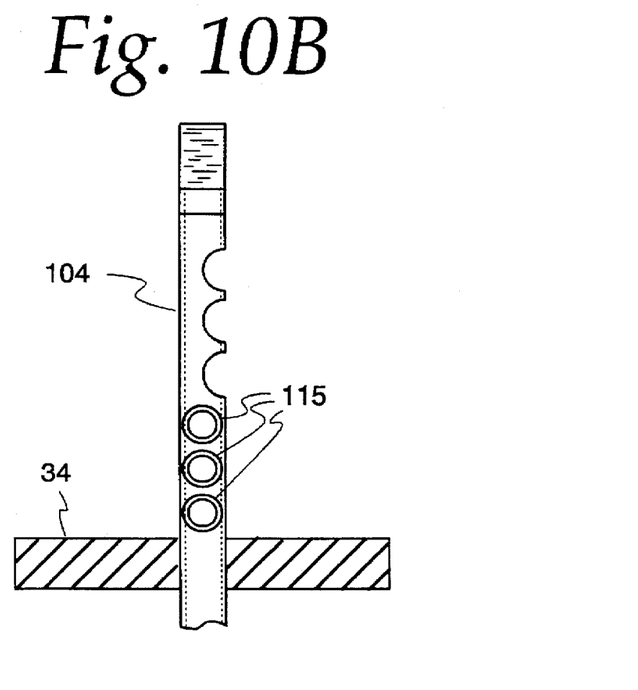

FIGS. 9A and 9B show a needle 104 having a slot therein impaled by the rubber 34 in the direction indicated by the arrow. As shown in FIG. 9B activation trials reveal that the rubber plug associated with conventional butt end needles was alleviated, however, rubber fragmentation 112 was still observed as illustrated. In order to solve the fragmentation issue, the slot was broken off into a series of narrower slots 114 as illustrated in FIGS. 10A and 10B, again showing impalement in the direction of the arrow indicated. In doing this, the rubber seal 34 was unable to penetrate the inner diameter of the needle, and produced insignificant small fragmentation 115, if any. The three slot design of FIGS. 10A and 10B may also be calculated with similar surface area to that of a standard needle inner diameter.

Figure 11A:
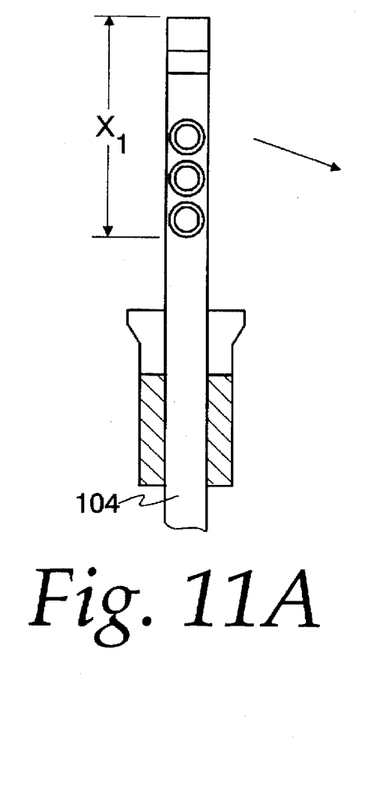
FIGS. 11A and 11B illustrate the collapse of the internal needle tip with the three-hole design.
Figure 11B:
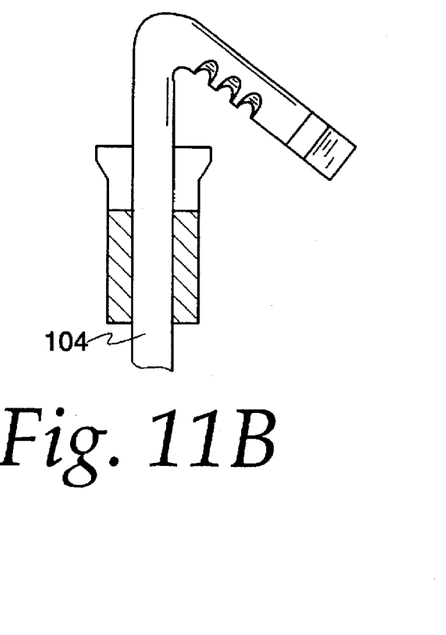
Figure 12:
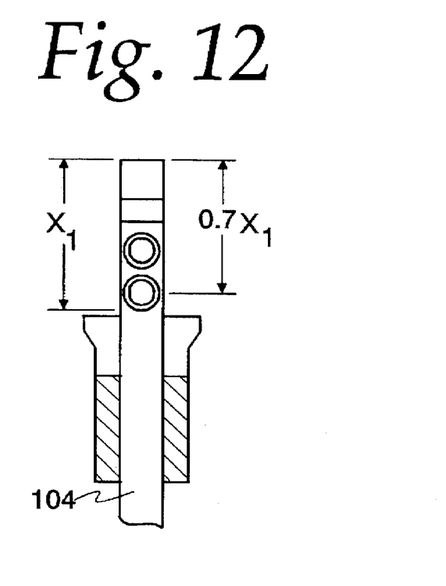
FIG. 12 illustrates the two-hole design of the preferred embodiment for internal tip side port geometry for the non-coring needle.

Initial testing gave inconsistent results, the predominate failure mode being that of the collapse of the entire butt end of the needle 104, as illustrated in the geometry of FIG. 11A and collapse shown in FIG. 11B. The collapse problem was due to excessive slot depth from the EDM process and excessive torque being applied to the butt end of the needles during activation. By modifying the position of the slots, as well as reducing the number of slots from three to two in the preferred embodiment, a shortened moment arm was achieved and the collapse of the butt end was eliminated, as shown in FIG. 12 wherein a 0.7 distance (X1) provides a shortened moment arm.

As discussed, success in avoiding collapse, also requires careful control of slot depth for the 29 gage needle of the embodiment, the slot depth preferably not exceeding ⅓ of the overall outer diameter of the needle. Activation trials proved successful, collapse of the butt end being eliminated. In addition, slots eliminated the large fragmentation sizes from 0.006" by 0.030" (0.14 mm×0.8 mm) to well below 100×100 microns (0.004") .

Figure 13:
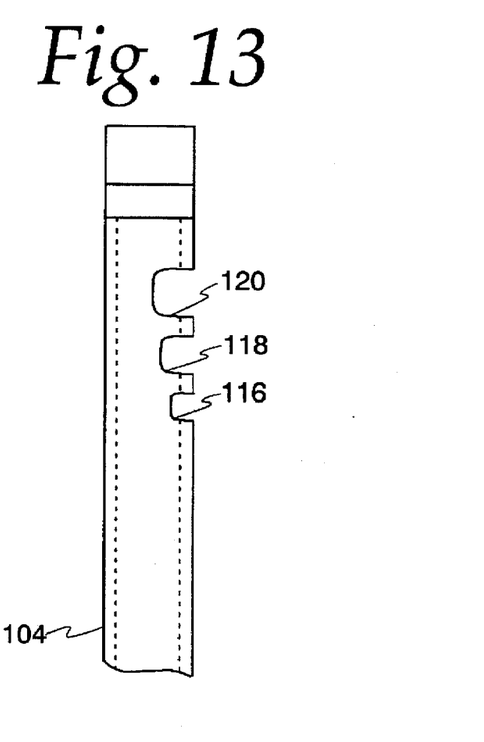
FIG. 13 illustrates an alternative side port geometry design wherein size and depth of openings are varied to alter flow characteristics.

FIG. 13 illustrates an alternative embodiment wherein multiple slots 116, 118 and 120 are provided at varying depth and sizes facilitating alternative or enhanced flow characteristics. FIG. 13 shows the slots 116, 118 and 120 in linear orientation relative to one another, however, staggering or shifting of the slots around the needle 104 may also prove useful.

While preferred embodiments of the invention have been shown and described for the automatic medicament injector employing non-coring needle, other embodiments of the present invention will be readily apparent to those skilled in the art from consideration of the specification in practice of the invention disclosed herein. While the needle is described with small gage needles, larger gage needles also give rise to coring problems, sometimes magnified as needle size increases, thus also benefitting from practice of the invention. Additionally, changing the size and number of the slots further facilitates control over the discharge rate of the medication, many medications requiring a slower rate of injection because of viscosity and pain reaction. It is intended therefore that the specification and examples be considered only as exemplary embodiments, with the true scope and spirit being indicated by the following claims.

What is claimed is:

1. A fluid injector comprising:
    (A) a tubular cartridge having an upper end and a lower end, said cartridge having an interior bore which widens at said lower end of said cartridge to form a needle housing assembly residence chamber for receiving a needle housing assembly;
    (B) a puncturable end cap sealing said lower end of said cartridge;
    (C) an ampule slidably disposed within the upper end of said cartridge bore, said ampule having an upper end and a lower end and being suitable for storing a fluid charge to be expelled therefrom;
    (D) a piston slidably seated within said upper end of said ampule;
    (E) a puncturable ampule end stopper rigidly attached to and sealing said lower end of said ampule;
    (F) a needle housing assembly slidably disposed within said upper end of said cartridge below said ampule, said needle housing assembly comprising:
        a generally cup-shaped housing having a housing bottom and flexible upstanding housing wall sections attached to the periphery of said housing bottom, said housing walls, extending toward said lower end of said ampule and said housing wall sections having upper edges for engaging with said lower end of said ampule,
        a hollow injection needle extending through and rigidly engaged by said housing bottom and having an internal section, and an external section, said internal section of said hollow injection needle extending from said housing bottom, upwardly within said housing walls, toward said puncturable ampule end stopper, and said external section of said hollow injection needle extending from said housing bottom downwardly toward said puncturable end cap of said cartridge without protruding from said puncturable end cap,
        the upper edges of said housing wall sections being engageable with said lower end of said ampule as said ampule slides downwardly within said cartridge bore, whereby actuation moves said ampule downwardly within said cartridge bore in said upper end of said cartridge toward said lower end of said cartridge thus engaging said upper edges of said housing wall sections and moving said needle housing assembly from said upper end of said cartridge into said needle housing assembly residence chamber at said lower end of said cartridge causing said external section of said hollow injection needle to protrude through said puncturable end cap and allowing said flexible housing wall sections to expand outwardly in said needle housing assembly residence chamber, the further downward movement of said ampule causing the internal section of said hollow injection needle to pass through said puncturable ampule end stopper thereby allowing fluid to be injected outwardly through said hollow injection needle; and
    (G) an actuator for engaging said tubular cartridge and for propelling said ampule toward said puncturable end cap and for propelling said piston within said ampule toward said ampule end stopper to inject a fluid.

2. A fluid injector according to claim 1, wherein said actuator (G) comprises:
    (i) an actuator housing having a first end and a second end, said first end for receiving said piston and said second end for operating said actuator;
    (ii) an elongated piston driver slidably seated in said actuator housing, said piston driver having a piston face for contacting said piston, a transfer surface for transferring propelling force from said actuator housing to said piston driver, and a trigger end for releasably engaging said second end of said actuator housing;
    (iii) a seat flange in said second end of said actuator housing for releasably engaging said piston driver;
    (iv) a release flange in said second end of said actuator housing on said piston driver for disengaging said piston driver from said second end;
    (v) a propulsion mechanism connected between said transfer surface and said second end of said housing for driving said piston driver toward said puncturable end cap when said piston driver is disengaged by said release flange.

3. A fluid injector as in claim 2, wherein the hollow injection needle is a non-corning hollow injection needle.

4. A fluid injector as in claim 3, wherein the non-coring hollow injection needle has an internal end section and an external end section, said internal end section of said non-coring hollow injection needle extending from said needle housing assembly toward said puncturable ampule end stopper, said non-coring hollow injection needle having a pressed closure at the tip of said internal end section and a sideport opening therebelow, thereby allowing medicament to be injected outwardly through said non-coring hollow injection needle via said sideport opening.

5. A fluid injector as in claim 2, wherein said propulsion mechanism is a spring connected between said transfer surface and said second end of said housing.

6. A fluid injector as in claim 1, further comprising locking means located at said actuator for preventing unintentional discharge of said fluid injector.

7. A fluid injector as in claim 6, wherein said locking means comprises a removable safety pin having a projection projecting into said actuator for preventing activation of said actuator.

8. A fluid injector as in claim 1, wherein the hollow injection needle is a non-coring hollow injection needle.

9. A fluid injector as in claim 8, wherein the non-coring hollow injection needle has an internal end section and an external end section, said internal end section of said non-coring hollow injection needle extending from said needle housing assembly toward said puncturable ampule end stopper, said non-coring hollow injection needle having a pressed closure at the tip of said internal end section and a sideport opening therebelow, thereby allowing medicament to be injected outwardly through said non-coring hollow injection needle via said sideport opening.

10. A fluid injector according to claim 1, wherein said needle housing assembly is provided with locking means for irreversibly locking said needle assembly housing to said ampule when said needle housing assembly and said ampule are a predetermined distance apart.

11. A fluid injector as in claim 1, wherein said external end of said injection needle is disposed within said puncturable end cap of said cartridge a sufficient distance to provide a microbe-impermeable seal without protruding therefrom.

12. An automatic medicament injector employing a non-coring needle, comprising:

a tubular cartridge having an upper end and a lower end with a cartridge bore defined by a cartridge bore wall extending between the upper end and the lower end, said lower end of said cartridge bore widening to form a needle housing assembly residence chamber for receiving a needle housing assembly;

an ampule slidably disposed within the upper end of said cartridge bore, said ampule having an upper end and a lower end and being suitable for storing a medicament charge to be expelled therefrom;

a puncturable ampule end stopper rigidly attached to and sealing said lower end of said ampule;

a piston contacting said ampule for driving said ampule in order to expel said medicament charge therefrom; and a needle housing assembly slidably disposed within said upper end of said cartridge below said ampule, said needle housing assembly comprising:

a generally cup-shaped housing having a housing bottom and flexible upstanding housing wall sections attached to the periphery of said housing bottom, said housing walls extending toward said lower end of said ampule and said housing wall having upper edges for engaging with a lower end of said ampule, a non-coring hollow injection needle extending through and rigidly engaged within the needle housing assembly and having an internal end section and an external end section, said internal end section of said hollow injection needle extending from said housing assembly toward said puncturable ampule end stopper, said hollow injection needle having a pressed closure at the tip of said internal end section and a sideport opening therebelow, and the upper edges of said housing wall sections being engageable with said lower end of said ampule as said ampule slides downwardly within said cartridge bore, whereby actuation moving said ampule within said cartridge bore in said upper end of said cartridge toward said lower end of said cartridge thus engages said housing and moves said needle housing assembly from said upper end of said cartridge into said needle housing assembly residence chamber at said lower end of said cartridge, the further downward movement of said ampule driven by said piston causing the pressed closure at the tip of said internal end section to pass through said puncturable ampule end stopper thereby allowing medicament to be injected outwardly through said non-coring needle via said sideport opening.

13. An automatic injector in accordance with claim 12 wherein said sideport opening below the tip of said internal end section comprises a plurality of slots in said internal end section of said hollow injection needle.

14. An automatic injector in accordance with claim 2 wherein said pressed closure comprises a crimp at the tip of said internal end section of said hollow injection needle providing a closure having rugged lacerations therein.

15. An automatic injector in accordance with claim 12 comprising an actuator for engaging said tubular cartridge and for propelling said ampule toward said non-corning hollow injection needle and for propelling said piston within said ampule toward said ampule end stopper to inject the medicament.

16. An automatic injector in accordance with claim 15, wherein said actuator comprises:

(i) an actuator housing having a first end and a second end, said first end for receiving said piston and said second end for operating said actuator;

(ii) an elongated piston driver slidably seated in said actuator housing, said piston driver having a piston face for contacting said piston, a transfer surface for transferring propelling force from said actuator housing to said piston driver, and a trigger end for releasably engaging said second end of said actuator housing;

(iii) a seat flange in said second end of said actuator housing for releasably engaging said piston driver;

(iv) a release flange in said second end of said actuator housing on said piston driver for disengaging said piston driver from said second end;

(v) a propulsion mechanism connected between said transfer surface and said second end of said housing for driving said piston driver toward said puncturable end cap when said piston driver is disengaged by said release flange.

* * * * *

UNITED STATES PATENT AND TRADEMARK OFFICE
CERTIFICATE OF CORRECTION

PATENT NO. : 5,709,668
DATED : January 20, 1998
INVENTOR(S) : Jonathan L. Wacks

It is certified that error appears in the above-indentified patent and that said Letters Patent is hereby corrected as shown below:

Column 12, line 67, change "non-corning" to --non-coring--.
Column 13, line 1, change "non-corning" to --non-coring--.
Column 13, lines 3-4, change "non-corning" to --non-coring--.
Column 13, line 6, change "non-corning" to --non-coring--.
Column 13, line 22, change "non-corning" to
   --non-coring--.
Column 13, line 23, change "non-corning" to --non-coring--.
Column 13, line 26, change "non-corning" to --non-coring--.
Column 13, line 28, change "non-corning" to --non-coring--.
Column 14, line 32, change "2" to --13--.

Signed and Sealed this

Nineteenth Day of May, 1998

BRUCE LEHMAN

Attest:

Attesting Officer

Commissioner of Patents and Trademarks